United States Patent
Kelly et al.

(10) Patent No.: US 6,646,183 B2
(45) Date of Patent: Nov. 11, 2003

(54) DNA ENCODING FOR A DISEASE RESISTANCE GENE FROM COMMON BEAN AND METHODS OF USE

(75) Inventors: James D. Kelly, Mason, MI (US); Maeli Melotto, Lansing, MI (US)

(73) Assignee: Board of Trustees operating Michigan State University, East Lansing, MI (US)

(*) Notice: Subject to any disclaimer, the term of this patent is extended or adjusted under 35 U.S.C. 154(b) by 0 days.

(21) Appl. No.: 09/838,955

(22) Filed: Apr. 20, 2001

(65) Prior Publication Data

US 2002/0056152 A1 May 9, 2002

Related U.S. Application Data

(60) Provisional application No. 60/199,064, filed on Apr. 20, 2000.

(51) Int. Cl.$^7$ .................... C12N 15/09; C12N 15/29; C12N 15/82; A01H 5/00; A01H 5/10
(52) U.S. Cl. .................... 800/279; 800/278; 800/298; 800/295; 800/313; 435/419; 435/468; 435/320.1; 536/23.6
(58) Field of Search .................... 800/279, 278, 800/298, 295, 313; 435/419, 468, 320.1; 536/23.6

(56) References Cited

PUBLICATIONS

Lazar et al. Molecular and Cellular Biology, vol. 8, No. 3, pp. 1247–1252 1988.*
Broun et al. Science, vol. 282, pp. 131–133, 1998.*
Ayres, N.M. et al., *Microsatellites and a single–nucleotide polymorphism differentiate apparent amylose classes in an extended pedigree of US rice germ plasm*, Theor. Appl. Genet. 94:773–781 (1997).
Balardin, R.S. et al., *Interaction between Colletotrichum lindemuthianum Races and Gene Pool Diversity in Phaseolus vulgaris*, J. Amer. Soc. 123(6):1038–1047 (1998).
Balardin, R.S. et al.; *Virulence and Molecular Diversity in Colletotrichum lindemuthianum from South, Central, and North America*; Phytopathology 87:1184–1191 (1997).
Balardin, R. S. et al.; *Identification of Race 65–Epsilon of Bean Anthracnose (Collectotrichum lindemuthianum) in Michigan*, Plant Dis. 80:712 (1996).
Bent, Andrew F., *Plant Disease Resistance Genes: Function Meets Structure*, The Plant Cell 8:1757–1771 (1996).
Dixon, Mark S. et al., *The Tomato CF–2 Disease Resistance Locus Comprises Two Functional Genes Encoding Leucine–Rich Repeat Proteins*, Cell 84:451–459 (1996).
Flor, H. H., *Host–Parasite Interaction In Flax Rust—Its Genetics And Other Implications*, Phytopathology 45:680–685 (1955).

Freyre, R. et al., *Towards an integrated linkage map of common bean. 4. Development of a core linkage map and alignment of RFLP maps*, Theor. Appl. Genet. 97:847–856 (1998).
Geffroy, V. et al., *A family of LRR sequences in the vicinity of the Co–2 locus for anthracnose resistance in Phaseolus vulgaris and its potential use in marker–assisted selection*, Theo. Appl. Genet. 96:494–502 (1998).
Hirokawa, T. et al., *SOSUI: classification and secondary structure prediction system for membrane proteins*, Bioinformatics 14:378–379 (1998).
Hofmann, Kay et al., *The PROSITE database, its status in 1999*, Nucleic Acids Research 27:215–219 (1999).
Jia, Yulin et al., *Alleles of Pto and Fen Occur in Bacterial Speck–Susceptible and Fenthion–Insensitive Tomato Cultivars and Encode Active Protein Kinases*, The Plant Cell 9:61–73 (1997).
Jones, David A. et al., *Isolation of the Tomato Cf–9 Gene for Resistance to Cladosporium fulvum by Transposon Tagging*, Science 266:789–793 (1994).
Kanazin, Vladimir et al., *Resistance gene analogs are conserved and clustered in soybean*, Proc. Natl. Acad. Sci. USA 93:11746–11750 (1996).
Kelly, James D. et al., *New Races of Colletotrichum lindemuthianum in Michigan and Implications in Dry Bean Resistance Breeding*, Plant Disease 78(9):892–904 (1994).
Kessell, Rick et al., *Recessive Resistance to Plasmopara lactucae–radicis Maps by Bulked Segregant Analysis to a Cluster of Dominant Disease Resistance Genes in Lettuce*, Mol. Pl. Microbe Interact. 6:722–728 (1993).
Lamb, Christopher J. et al., *Signals and Transduction Mechanisms for Activation of Plant Defenses against Microbial Attack*, Cell 56:215–224 (1989).
Li, Zhaohui et al., *The ltk gene family encodes novel receptor–like kinases with temporal expression in developing maize endosperm*, Plant Mol. Bio. 37:749–761 (1998).
Maisonneuve, B. et al., *Rapid mapping of two genes for resistance to downy mildew from Lactuca serriola to existing clusters of resistance genes*, Theor. Appl. Genet. 89:96–104 (1994).
Martin, Gregory B. et al., *A Member of the Tomato Pto Gene Family Confers Sensitivity to Fenthion Resulting in Rapid Cell Death*, The Plant Cell 6:1543–1552 (1994).

(List continued on next page.)

Primary Examiner—Elizabeth F. McElwain
Assistant Examiner—Medina A. Ibrahim
(74) Attorney, Agent, or Firm—Harness, Dickey & Pierce, P.L.C.

(57) ABSTRACT

The present invention provides novel purified and isolated nucleic acid sequences associated with disease resistance and tolerance in plants. Methods of using the nucleic acid sequences to confer disease resistance and tolerance to plants are also provided.

24 Claims, 7 Drawing Sheets

PUBLICATIONS

Figure 3A:
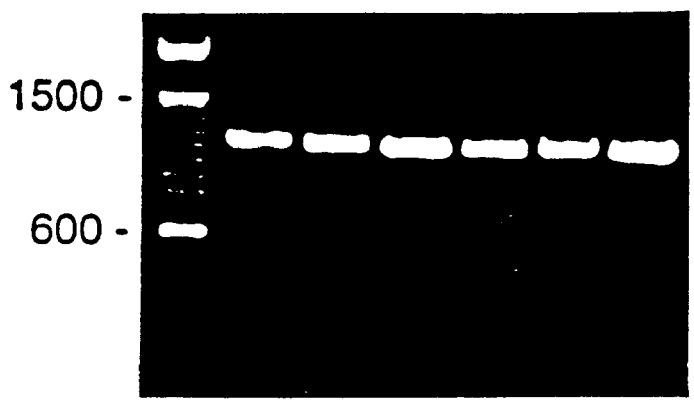
Figure 3B:
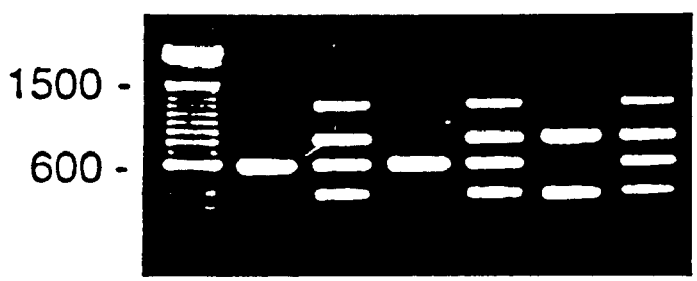
Figure 3C:
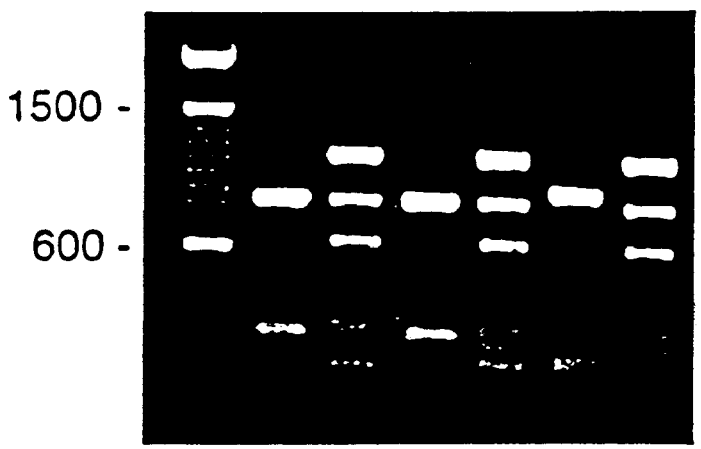
Figure 3D:
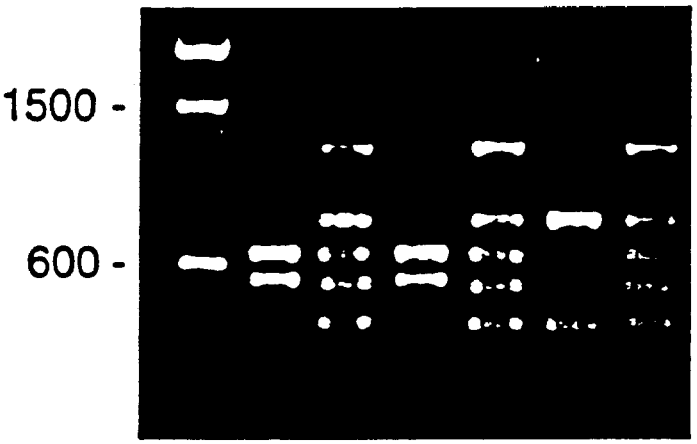

Martin, Gregory B. et al., *Map–Based Cloning of a Protein Kinase Gene Conferring Disease Resistance in Tomato*, Science 262:1432–1436 (1993).

Melotto, M. et al., *Development of a SCAR marker linked to the I gene in common bean*, Genome 39:1216–1219 (1996).

Meyers, Blake C. et al., *The Major Resistance Gene Cluster in Lettuce Is Highly Duplicated and Spans Several Megabases*, The Plant Cell 10:1817–1832 (1998).

Michelmore, R. W., *Identification of markers linked to disease–resistance genes by bulked segregant analysis: A rapid method to detect markers in specific genomic regions by using segregating populations*, Proc. Natl. Acad. Sci. USA 88:9828–9832 (1991).

Pastor–Corrales, Marcial Antonio et al., *Inheritance of Anthracnose Resistance in Common Bean Accession G 2333*, Plant Disease 78:959–962 (1994).

Rivkin, M. et al., *Disease–resistance related sequences in common bean*, Genome 42:41–47 (1999).

Scofield, Steven R. et al., *Molecular Basis of Gene–for–Gene Specificity in Bacterial Speck Disease of Tomato*, Science 274:2063–2065 (1996).

Suiter, Karl A. et al., *Linkage–1: a PASCAL computer program for the detection and analysis of genetic linkage*, J. Hered. 74:203–204 (1983).

Tang, Xiaoyan et al., *Initiation of Plant Disease Resistance by Physical Interaction of AvrPto and Pto Kinase*, Science 274:2060–2063 (1996).

van der Knaap, Esther et al., *Identification of a Gibberellin–Induced Receptor–Like Kinase in Deepwater Rice (Accession No. Y07748)*. Plant Physiol. 112:1397–1400.

Walker, John C., *Structure and function of the receptor–like protein kinases of higher plants*, Pl. Mol. Biol. 26:1599–1609 (1994).

Young, Roberto A. et al., *RAPD Markers Linked to Three Major Anthracnose Resistance Genes in Common Bean*, Crop Science 37:940–946 (1997).

Young, Roberto A. et al., *Chracterization of the Genetic Resistance to Colletotrichum lindemuthianum in Common Bean Differential Cultivars*, Plant Dis. 80:650–654 (1996).

Young, R. A. et al., *Marker–assisted dissection of the oligogenic anthracnose resistance in the common bean cultivar, G 2333*, Theor. Appl. Genet. 96:87–94 (1998).

Yu, Yong G. et al., *Isolation of a superfamily of candidate disease–resistance genes in soybean based on a conserved nucleotide–binding site*, Proc. Natl. Acad. Aci. USA 93:11751–11756 (1996).

\* cited by examiner

Figure 1A

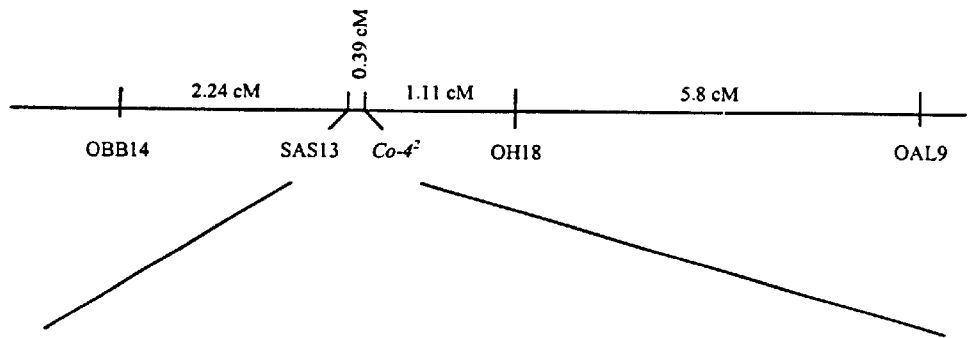

Figure 1B

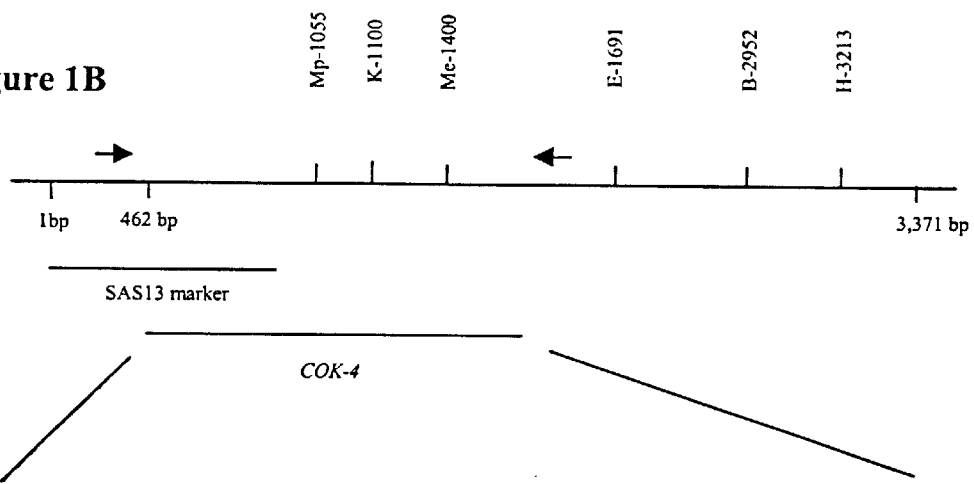

Figure 1C

1    MFLNCVGMCCSKPTTNTTSSQRQFPTLIEELCHQFSLTDLRKATNNFDQKRV
53   IGSGLFSEVYKGCLQHDGASDYTVAIKRFDYQGWAAFNKEIELLCQLRHPRCVSLIGFCNHE
115  NEKILVYEYMSNGSLDKHLQEGQLSWKKRLEICIGVARGLHFLHTGAKRSI
166  FHCILGPGTVLLDDQMEPKLAGFDASEQGSRFMSKQKQINVIVFWVIFVLLYELTHCHDF
226  LWIKLSLLFVIGCRGYTATDYLMDGIITAKWDVFSFGFLLLEVVCRRMFYLIT
279  LTKKECLENPVEERIDPIIKGKIAPDCWQVFVDMMVSCLKYEPDERPTIGEVEVQLEHALSMQE
343  QSDITNSNSEYTLLSKTIISLGVKKCK•

Figure 2

```
a)   1  MFLNCVGMCCSKPTTNTTSSQRQFPTLIEELCHQFSLTDLRKATNNFDQKRVIGSGLFSEVYKGCLQHDG
b)   9                    TNSINDALSSSYLVPFESYRVPLVDLEEATNNFDHKFLIGHGVFGKVYKGVLR-DG
c)   1          MGSKYSKATNSISDASNSFES------YRFPLEDLEEATNNFDDKFFIGEGAFGKVYKGVLR-DG
d)  27                                  YRVPFVDLEEATNNFDDKFFIGEGGFGKVYRGVLR-DG
e) 564  NVNGGAAASETYSQASSGPRDIHVVETGNMVISIQVLRNVTNNFSDENVLGRGGFGTVYKGEL-HDG
f) 513                                         ATNNFSSANKLGRGGFGTVYKGRLL-DG a) ASDYTVAIKRFDY-----QGWAAFNKEIELLCQLRHPRCVSLIGFCNHENEKILVYEYMSNGSLDKHL----QEG
b) AKVALKRRTPESS-----QGIEEFETEIETLSFCRHPHLVSLIGFCDERNEMILIYKYMENGNLKRHL----YGS
c) TKVALKRQNRDSR-----QGIEEFGTEIGILSRRSHPHLVSLIGYCDERNEMVLIYDYMENGNLKSHL----TGS
d) TKVALKKHKRESS-----QGIEEFETEIEILSFCSHPHLVSLIGFCDERNEMILIYDYMENGNLKSHL----YGS
e) TK---IAVKRMEAGVMGNKGLNEFKSEIAVLTKVRHRNLVSLLGYCLDGNERILVYEYMPQGTLSQHL----FEW
f) KEIAVKRLSKMSL-----QGTDEFKNEVKLIARLQHINLVRLIGCCIDKGEKMLIYEYLENLSLDSHIFDITRRS a) Q------L-----SWKKRLEICIGVARGLHFLHTGAKRSIFHCILGPGTVLLDDQMEPKLAGFD---ASEQGSRF
b) D------LPTMSMSWEQRLEICIGAARGLHYLHT---RAIIHRDVKSINILLDENFVPKITDFG---ISKKGT--
c) D------LPSM--SWEQRLEICIGAARGLHYLHT---NGVMHRDVKSSNILLDENFVPKITDFG---LSKTRPQ-
d) D------LPTMSMSWEQRLEICIGAARGLHYLHT---NGVIHRDVKCTNILLDENFVPKITDFG---ISKTMPEL
e) KEHNLRPL-----EWKKRLSIALDVARGVEYLHSLAQQTFIHRDLKPSNILLGDDMKAKVADFGLVRLAPADGKC
f) N------L-----NWQMRFDITNGIARGLVYLHRDSRFMIIHRDLKASNVLLDKNMTPKISDFG---MARIFGRD a) MSKQKQINVIVFWVIFVLLYELTHCHDFLWIKLSLLFVIGCRGYTATDYLMDGIITAKWDVFSFGFLLLEVVCR
b) ------------ELDQTH------LSTV-VKGTLGYIDPEYFIKGRLTEKSDVYSFGVVLFEVLCA
c) ------------LYQTTD---------VKGTFGYIDPEYFIKGRLTEKSDVYSFGVVLFEVLCA
d) ----------------DLTH--------LSTV-VRGNIGYIAPEYALWGQLTEKSDVYSFGVVLFEVLCA
e) VSVETRL----------------------------AGTFGYLAPEYAVTGRVTTKADVFSFGVILMELITG
f) DAEANTRK--------------------------VVGTYGYMSPEYAMDGIFSMKSDVFSFGVLLLEIISG a) R-M---------FY-------LIT-LTKK--------E---CLEN-PVEERIDPII--K-GKIAPDCWQVF--
b) R-S---------AI-------VQS-LPREMVNLAEWAVE---SHNNGQLEQIVDPNL--A-DKIRPESLRKF--
c) R-S---------AM-------VQS-LPREMVNLAEWAVE---SHNNGQLEQIVDPNL--A-DKIRPESLRKF--
d) RPA---------LY-------LSE-MMSS---------DDETQKMG-QLEQIVDPAI--A-AKIRPESLRMF--
e) R-KALDETQPEDSMH------LVTWFRRM---------Q---LSKD-TFQKAIDPTI--DLTEETLASVSTV--
f) K-KNNG------FYNSNQDLNLLA-LVWR---------K---WKEG-KWLEILDPIIIDS-SSSTGQAHEILRC a) VDMMVSCLKYEPDERPTIGEVEVQLEHALSMQEQSDITNSNSEYTLLSKTIISLGVKKCK    369
b) GDTAVKCLALSSEDRPSMGDVLWKLEYALRLQE                              318
c) GETAVKCLALSSEDRPSMGDVLWKLEYALRLQE                              308
d) GETAMKCLAPSSKNRPSMGDVLWKLEYALCLQE                              312
e) AELAGHCCAREPHQRPDMGHAVNVLSTLSDVWKPSDPDSDDS                     902
f) IQIGLLCVQERAEDRPVMASVMVMI                                      792
```

Figure 4A

```
A)   1    atgtttctgaattgtgtgggcatgtgttgttcgaagcccacaacaaatacaacttcatct
B)        atgtttctgaattgtgtgggcatgtgttgttcgaagcccacaacaaatacaacttcatct
C)        atgtttctgaattgtgtgggcatgtgttgtacgaagcccacaacaaatacaacttcatct A)   61   cagagacagtttccaacgttgatagaagagctgtgccatcaattttctctcaccgatctt
B)        cagagacagtttccaacgttgatagaagagctgtgccatcaattttctctcaccgatctt
C)        cagagacagtttccaacgttgatagaagagctgtgccatcaattttctctctccgatctt A)   121  aggaaagccaccaataactttgatcagaagagagtaataggaagtggattatttagtgaa
B)        aggaaagccaccaataactttgatcagaagagagtaataggaagtggattatttagtgaa
C)        aggaaagccatcaataactttgatcagaagagagtaataggaagtggatttttagggaa A)   181  gtatacaaagggtgtctgcagcacgatggtgcttctgattacacggtcgcaataaagcga
B)        gtatacaaagggtgtctgcagcatgatggtgcttctgattacacggtcgcaataaagcga
C)        gtatattaagggtgtctgcagcatgatggtgcttctgattacacggtcgcaataaagcga A)   241  tttgattatcaaggatgggcagcgttcaacaaggaaatcgaattgctatgccagcttcgt
B)        tttgattatcaaggatgggcagcgttcaacaaggaaatcgaattgctatgccagcttcgt
C)        tttgattatcaaggatgggaagcgttcaacaaggaaatcgaattgctatgccagcttcgt A)   301  caccctagatgtgtttctcttataggattctgcaaccacgaaaatgagaagattcttgta
B)        caccctagatgtgtttctcttataggattcagcaaccacgaaaatgagaagattcttgta
C)        caccctagatgtgtttctcttataggattctgcaaccaccaaaatgagaagattcttgta A)   361  tacgagtacatgtccaatggatctctagataaacacctacaagaaggtcaactatcatgg
B)        tacgagtacatgtccaatggatctctagataaacacctacaagaaggtcaactatcatgg
C)        tacgagtacatgtccaatggatctctagataaacacctacaagatggtgaactatcatgg A)   421  aagaagaggctggagatatgcataggagtagcacgtggactacacttccttcacaccgga
B)        aagaagaggctagagatatgcataggagtagcacgtggactacactaccttcacaccgga
C)        aagaagaggctagagatctgcataggagtagcacgtggactacactaccttcacactggt A)   481  gccaagcgttccatctttcactgtatcctcggtcctggtaccgtccttttggatgaccag
B)        gccaagcgttccatctttcactgtatcctcggtcctggtaccgtccttttggatgaccag
C)        gccaagcgttccatctttcactgtatcctcggtcctagtaccatccttttggatgaccaa A)   541  atggagccaaaactcgctggtttcgatgctagcgagcagggatcacgttttatgtcaaag
B)        atggagccaaaactcgctggtttcggtgctagcgagcagggatcacgttttatgtcaaag
C)        atggagccaaaactcgctggtttcggtgttagcatgcagggatcacgttttatgtcaaag A)   601  cagaagcaaatcaatgt-gatcgtgttttgggtaattttgtttgttgtatgagctcac
B)        cagaagcaaatcaatgtagatcgtgttttgggtaatttttgttttttgtatgagctcac
C)        cagaagcaaatcaatgtagatcgtgttttgggtaatttttgttttgttgtatgagctcac
```

Figure 4B

```
A) 660    tcactgccatgattttttgtggatcaaactaagct--tactctttgttataggttgtagggg
B)        tcactgccatgattttttgtggatcaaactaagct--tactctttgttataggttgttggggg
C)        tcactgcaatgaattttttgtggatcaaactaagctaatactctttgttataggtacttttgg A) 720    ctacacggctacggactatctcatggatggtatcatcacagctaaatgggatgttttctc
B)        ctacacggctacggactatctcatggatggtatcatcacagctaaatgggatgttttctc
C)        ctaccccggctacggactatgtcatggatggtaccatcacagctaaatgggatgttttctc A) 780    atttggtttccttctactagaagttgtgtgcaggaggatgttttatttaataactctgac
B)        atttggtttccttctactagaagttgtgtgcaggaggatgttttatttgataactctgac
C)        atttggtttccttctactagaagttgtgtgcaggaggatgttttatttgataactctgac A) 840    taaaaaagaatgtctggagaatcctgttgaggagagaattgatccgattatcaaaggaaa
B)        taaaaaaaaatgtctggagaatcctgttgagtagagaattgatccgattatcaaagggaa
C)        taaaaaaaaatgtctggagaatcctgttgaggagagaattgatccgattatcaaagggaa A) 900    gattgcaccagattgttggcaagtgtttgtagatatgatggtaagttgcttgaagtatga
B)        gattgcaccagattgttggcaagtgtttgtagatatgatggtaacttgcttgaagtataa
C)        gattgcaccagattgttggcaagtgtttgtagatatgatggtaacttgcttgaagtatga A) 960    accagatgagagaccaacaattggtgaagtggaggtgcaacttgagcatgctctatccat
B)        accagatgagagaccaacaattggtgaagtggaggtgcaacttgagcatgctctatccat
C)        accagatgagcgaccaacaattggtgaagtggaggtgcaacttgagcatgctctatccat A) 1020   gcaggaacaatctgatatcacaaactccaactctgagtataccttactctccaaaaccat
B)        gcaggaacaagctgatatcacaaactccaactctgagtatactttactgtccaaaaccat
C)        gcaggaacaagctgatatcacaaactccaactctgagtataccttactgtccaaaaccat A) 1080   tatttcccttggagtgaagaaatgtaagtga  1110
B)        tatttccctgggagtgaagaaatgtaagtga
C)        tatttccc
```

DNA ENCODING FOR A DISEASE RESISTANCE GENE FROM COMMON BEAN AND METHODS OF USE

CROSS REFERENCE TO RELATED APPLICATION

This application claims benefits of Provisional Application 60/199,064, filed Apr. 20, 2000.

SPONSORSHIP

Work on this invention was sponsored in part by United States Agency for International Development Grant DAN 1310-G-SS-6008-00. The Government may have certain rights in the invention.

FIELD OF THE INVENTION

The invention relates generally to disease resistance genes from plants and more particularly to anthracnose resistance genes from legumes.

BACKGROUND OF THE INVENTION

Plants can be damaged by a wide variety of pathogenic organisms including viruses, bacteria, fungi and nematodes. Annual crop losses due to these pathogens is in the billions of dollars. Synthetic pesticides are one form of defense against pathogens and each year thousands of tons of such chemicals are applied to crops. However, there are concerns regarding the short term and long term environmental damage due to chemical pesticides use, as well as inherent risks to human health.

Plants also contain their own innate mechanisms of defense against pathogenic organisms. Natural variation for resistance to plant pathogens has been identified by plant breeders and pathologists and bred into many crop plants. These natural disease resistance genes often provide high levels of resistance to pathogens and represent the most economical and environmentally friendly form of crop protection.

Genetic resistance is the most efficient way to control anthracnose, the disease caused by the fungus *Colletotrichum lindemuthianum*, in common bean (*Phaseolus vulgaris* L.). The high genetic variability observed in the pathogen population (Balardin, R. S. et al., Phytopathology 87:1184–1191 (1997)) is associated with different resistance genes present in the host (Balardin, R. S. et al., J. Amer. Sco. Hort. Sci. 123(6):1038–1047 (1998)). Seven independent dominant disease resistance genes (Co-1 to Co-7) controlling anthracnose in bean have been described (Balardin, R. S. et al., Phytopathology 87:1184–1191 (1997)). Each of these genes confers resistance to certain races of the pathogen strongly suggesting that resistance to anthracnose in common bean follows the gene-for-gene theory (Flor, H. H., Phytopathology 45:680–685 (1947)). Certain resistance genes are more effective than others in controlling multiple races of the pathogen (Balardin, R. S. et al., J. Amer. Sco. Hort. Sci. 123(6):1038–1047 (1998)).

The bean breeding line SEL 1308 derived from the highly resistant differential cultivar G2333, is known to possess the single dominant Co-42 gene for anthracnose resistance (Young, R. A. et al., Theor. Appl. Genet. 96:87–94 (1998)). When inoculated with 34 selected races of *C. lindemuthianum* chosen to represent a diverse sample of the pathogen population, SEL 1308 demonstrated a resistance index (RI) of 97% (Balardin, R. S. et al., J. Amer. Sco. Hort. Sci. 123(6):1038–1047 (1998)). The only cultivar with a higher RI (100%) was G2333 known to possess the combination of three independent resistance genes, Co-42, Co-5, and Co-7 (Young, R. A. et al., Theor. Appl. Genet. 96:87–94 (1998)). This three-gene combination confers resistance to all described races of the pathogen (Pastor-Corrales, M. A. et al., Plant Dis. 78:959–962 (1994)). Among the reported resistance genes, the Co-42 gene in SEL 1308 exhibits the broadest-based resistance in common bean (Balardin, R. S. et al., J. Amer. Sco. Hort. Sci. 123(6):1038–1047 (1998)).

Although plants can be bred for disease resistance traits, this can be a long and tedious process. A conventional plant breeding program requires as much as ten years to develop a new variety. Furthermore, once a new variety is introduced, it may not prove resistant to new forms of the pathogen it was selected to be resistant to. For example, new races of *C. lindemuthianum* pathogenic to current commercial varieties of dry bean have been identified (Balardin, R. S. et al., Plant Dis. 80:712 (1996); Kelly, J. D. et al., Plant Disease 78:892–894 (1994)). Sources of resistance to anthracnose in adapted commercial bean varieties grown in the U.S. are ineffective against these races (Kelly, J. D. et al., Plant Disease 78:892–894 (1994)), whereas new resistance sources in Mexican germplasm offers an effective solution for the control of anthracnose (Pastor-Corrales, M. A. et al., Plant Dis. 78:959–962 (1994)). For instance, resistance in the Mexican landrace variety G 2333 to 450 races of anthracnose is conditioned by a combination of three independent resistance genes (Co-42, Co-5, Co-7; Pastor-Corrales, M. A. et al., Plant Dis. 78:959–962 (1994); Young, R. A. et al., Crop Sci. 37:940–946 (1997)).

It would thus be desirable to provide disease resistant genes from legumes. No disease resistance gene has been cloned from the bean species *P. vulgaris* or any related legume species. It would further be desirable to provide genes associated with resistance to anthracnose. The Co-42 gene is a valuable candidate gene for molecular cloning due to its broad resistance and availability of a tightly linked marker (Young, R. A. et al., Theor. Appl. Genet. 96:87–94 (1998)). In common bean and soybean, resistance genes analogs (RGAs) have been identified using primers specific to conserved regions of known resistance genes and mapped close to known disease resistance locus (Kanazin, V. et al., PNAS (USA) 93:11746–11750 (1996); Yu, Y. G. et al., PNAS (USA) 93:11751–17756 (1996); Geffroy, V. et al., Theor. Appl. Genet. 96:494–502 (1998); Rivkin, M. I. et al., Genome 42:41–47 (1999)). Mapping of RGAs has been the only approach used to isolate known resistance gene sequences from common bean. RGAs, however, are not always closely associated with a resistance phenotype and may be loosely linked to known resistance locus limiting their value in chromosome walking to the gene. Additional approaches, such as map-based cloning are still needed to isolate resistance gene candidates in crop species. It would also be desirable to provide legume plants with disease resistance, preferably to anthracnose. It would be further desirable to transform plants using anthracnose resistant genes to produce disease resistant plants.

SUMMARY OF THE INVENTION

The present invention provides novel purified and isolated nucleic acid sequences associated with disease resistance in common bean (*Phaseolus vulgaris* L.). The DNA for COK-4 isolated from strain SEL 1308 is set forth in SEQ ID NO: 1 while the DNA for COK-4 isolated from *P. vulgaris* Black Magic is set forth in SEQ ID NO: 2. The deduced amino acid sequence of COK-4 is also provided and set forth in SEQ ID NO: 3. The predicted COK-4 protein contains a serine-threonine kinase domain with a highly hydrophobic membrane-spanning region.

Methods for making and using the DNA's encoding for COK-4 are also provided. For example, COK-4 may be used to provide plants with disease resistance, preferably to anthracnose. Vectors containing the DNA, transgenic plants and other organisms, e.g., *E. coli*, transfected with said vectors, as well as seeds from said plants, are also provided by the present invention. Additional objects, advantages, and features of the present invention will become apparent from the following description and appended claims, taken in conjunction with the accompanying drawings.

BRIEF DESCRIPTION OF THE DRAWINGS

The various advantages of the present invention will become apparent to one skilled in the art by reading the following specification and subjoined claims and by referencing the following drawings in which:

FIG. 1A is a schematic of the linkage map of the Co-42 locus showing the position of the molecular markers;

FIG. 1B is a schematic of the genomic region containing the Co-42 locus showing the contig developed from overlapping genomic clones;

FIG. 1C is the amino acid sequence for COK-4 (SEQ ID NO: 3);

FIG. 2 is a comparison of the COK-4 and other reported plant serine-threonine kinases amino acid sequences (SEQ ID NO: 3, 5–9);

FIGS. 3A–3D are photographs of agarose gels showing restriction analysis of COK-4 amplified in several genotypes;

FIGS. 4A–4B show a comparison of the DNAs of COK-4 homologues (SEQ ID NOS: 1, 2 and 4).

FIG. 5 is an autoradiograph of a Southern blot of Eco RI digested genomic DNA from bean cultivar and a BAC clone hybridized with the COK-4 gene; and FIG. 6 is a photograph of an agarose gel showing the DNA amplification of six bean cultivars with OBB14 and OH181150 RAPD markers;

DETAILED DESCRIPTION OF THE PREFERRED EMBODIMENTS

The present invention provides novel isolated nucleic acid sequences conferring disease resistance to plants. The DNA sequences encoding for COK-4 and conferring disease resistance isolated from *Phaseolus vulgaris* L. are set forth in SEQ ID NO: 1 (strain SEL 1308) and SEQ ID NO: 2 (strain TO). The deduced amino acid sequence is provided in SEQ ID NO: 3. The COK-4 protein has a serine-threonine kinase domain, which includes a protein kinase ATP-binding region signature (amino acids 53 to 79 of SEQ ID NO: 3), a primary transmembrane domain (amino acids 202 to 224 of SEQ ID NO: 3; FIG. 1C), putative sites for N-myristoylation and N-glycosylation, and a cAMP- and cGMP-dependent protein kinase site (amino acids 41 to 44 of SEQ ID NO: 3; FIG. 1C).

In one embodiment, the COK-4 nucleic acid sequences capable of conferring disease resistance or tolerance to plants can be distinguished from non-resistance conferring sequences by restriction mapping. For example, restriction patterns were polymorphic among three bean cultivars known to possess different alleles at the CO-4 locus. Perfect co-segregation between restriction patterns and disease resistance phenotype was observed in 1350 F3 individuals. Preferably, a COK-4 nucleotide sequence capable of conferring disease resistance to plant will have no more than two restriction sites for restriction enzymes Kpn I, Mse I or Msp I, whereas sequences associated with non-resistance to disease will have at least two restriction sites. For example, the nucleotide sequence of SEQ ID NO: 1 has one restriction site for Kpn I, Mse I or Msp I (Lane 2, FIGS. 3B–3D). Likewise, the nucleotide sequence of SEQ ID NO: 2 has one restriction site for Kpn I, Mse I, and Msp I (Lane 6, FIGS. 3B–3D). In contrast, the COK-4 nucleotide sequence associated with non-resistance to plant diseases (SEQ ID NO: 4) has at least two restriction sites for Kpn I and three sites for Mse I and Msp I (Lane 7, FIGS. 3B–3D).

In another embodiment the sequences of the present invention conferring disease resistance or tolerance to a plant can be incorporated in plant or bacteria cells using conventional recombinant DNA technology. Generally this involves inserting the DNA molecule into an expression system, wherein the DNA molecule is inserted into the expression system or vector in proper orientation and correct reading frame. The vector contains the necessary elements for the transcription and translation of the inserted protein-coding sequences. A large number of vector systems known in the art can be used, such as, but not limited to, plasmids, bacteriophage virus or other modified viruses. The DNA sequences are clones into the vector using standard cloning procedures in the art.

The method of conferring disease resistance or tolerance to a plant includes the steps of introducing an expression vector comprising cDNA encoding a COK-4 protein associated with disease resistance or a functional mutant thereof, operably linked to a promoter functional in a plant cell into the cells of plant tissue and expressing the encoding protein in an amount effective to render the plant tissue resistant or tolerant to disease. The choice of promoter will depend on the host cell system into which the gene is to be incorporated and the amount of protein expression desired. The level of expression can be increased by either combining the cDNA with a promoter that provides for a high level of expression, or by introducing multiple copies into the cell so that multiple copies are integrated into the genome of transformed plant cells. Once transferred cells exhibiting disease resistance or tolerance are obtained, transgenic plants and seeds can then be regenerated therefrom, and evaluated for stability of the inheritance of the disease resistance or tolerance trait.

Alternatively, seeds, seedlings or plants can be transformed directly with the nucleic acid sequences and expression vectors of the present invention. The most common methods for transforming plants are, by way of non-limiting example, Agrobacterium-mediated gene delivery, microprojectile bombardment, free DNA delivery to protoplasts and electrophoretic transformation. Preferably, the low-voltage transformation method described in U.S. Ser. No. 09/206,852 (incorporated by reference) is used to transform plants using the nucleic acid sequences of the present invention. This method utilizes low amperage current to deliver DNA into the meristematic cells and tissue of plants and plant seedlings.

A COK-4 nucleotide sequence associated with disease resistance may thus be fused to a gene or fragment thereof, which allows it to be expressed in a plant cell. The COK-4 nucleotide sequence in combination with the gene or gene fragment, is referred to as an "expression vector" herein. It will be appreciated that the expression vectors of the present invention may contain any regulatory elements necessary and known to those skilled in the art for expression of COK-4. For example, such vectors may contain, but are not limited to, sequences such as promoters, operators and regulators, which are necessary for and/or may enhance the expression of COK-4.

In another embodiment, the nucleic acid sequences of the present invention are used to genetically engineer plants to confer disease resistance or tolerance. Preferably, the plants genetically altered with the nucleic acid sequences of the present invention are of the Leguminosae family. This family includes, but is not limited to, peas, beans, chickpeas and peanuts. More preferably, the plants are of the genus Phaseolus and most preferably are from the common bean group, *Phaseolus vulgaris*. Non-limiting examples of common bean are green bean, kidney bean, snap bean, haricot, runner bean, wax bean, black bean and pinto bean.

In a further embodiment, the nucleic acid sequences of the present invention are used to genetically engineer plants which are resistant or tolerant to fungal diseases. Non-limiting examples of plant fungal diseases are rust and root rot. Preferably, the genetically engineered plants of the present invention will be resistant or tolerant to the fungal disease *Collectotrichum lindemuthianum*, commonly known as anthracnose.

As referred to herein, the term "cDNA" is meant a nucleic acid, either naturally occurring or synthetic, which encodes a protein product. The term "nucleic acid" is intended to mean natural and/or synthetic linear, circular and sequential arrays of nucleotides and nucleosides, e.g., cDNA, genomic DNA (gDNA), mRNA, and RNA, oligonucleotides, oligonucleosides, and derivatives thereof. The term "encoding" is intended to mean that the subject nucleic acid may be transcribed and translated into either the desired polypeptide or the subject protein in an appropriate expression system, e.g., when the subject nucleic acid is linked to appropriate control sequences such as promoter and enhancer elements in a suitable vector (e.g., an expression vector) and when the vector is introduced into an appropriate system or cell. As used herein, "polypeptide" refers to an amino acid sequence which comprises both full-length protein and fragments thereof.

As referred to herein, the term "capable of hybridizing under high stringency conditions" means annealing a strand of DNA complementary to the DNA of interest under highly stringent conditions. Likewise, "capable of hybridizing under low stringency conditions" refers to annealing a strand of DNA complementary to the DNA of interest under low stringency conditions. In the present invention, hybridizing under either high or low stringency conditions would involve hybridizing a nucleic acid sequence (e.g., the complementary sequence to SEQ ID No. 1 or portion thereof, with a second target nucleic acid sequence. "High stringency conditions" for the annealing process may involve, for example, high temperature and/or lower salt content, which disfavor hydrogen bonding contacts among mismatched base pairs. "Low stringency conditions" would involve lower temperature, and/or higher salt concentration than that of high stringency conditions. Such conditions allow for two DNA strands to anneal if substantial, as is the case among DNA strands that code for the same protein but differ in sequence due to the degeneracy of the genetic code. Appropriate stringency conditions which promote DNA hybridization, for example, 6× SSC at about 45° C., followed by a wash of 2× SSC at 50° C., are known to those skilled in the art or can be found in Current Protocols in Molecular Biology, John Wiley & Sons, NY (1989), 6.31–6.3.6. For example, the salt concentration in the wash step can be selected from a low stringency of about 2× SSC at 50° C., to a high stringency of about 0.2× SSC at 50° C. In addition, the temperature in the wash step can be increased from low stringency at room temperature, about 22° C., to high stringency conditions, at about 65° C. Other stringency parameters are described in Maniatis, T., et al., Molecular Cloning: A Laboratory Manual, Cold Spring Harbor Laboratory Press, Cold Spring N.Y., (1982), at pp. 387–389; see also Sambrook J. et al., Molecular Cloning: A Laboratory Manual, Second Edition, Volume 2, Cold Spring Harbor Laboratory Press, Cold Spring, N.Y. at pp. 8.46–8.47 (1989).

The foregoing and other aspects of the invention may be better understood in connection with the following examples, which are presented for purposes of illustration and not by way of limitation.

SPECIFIC EXAMPLE 1

Isolation and Characterization of the COK-4 Gene

Materials and Methods

Genetic analysis of the segregating population. The bean breeding line SEL 1308 obtained from CIAT was used as the source of the Co-42 gene. This line was derived from a backcross between the anthracnose susceptible cultivar Talamanca and the recurrent parent Colorado de Teopisca (accession number G2333). SEL 1308 was crossed to Black Magic, a susceptible black bean cultivar. Hybrid seeds were advanced to the F2 generation and a population of 1018 F2 individuals was developed. Progeny tests were performed in 96 F2 derived F3 families to discriminate homozygous from heterozygous resistant genotypes. Race 73 (ATCC 96512) of *C. lindemuthianum* was chosen to confirm the dominant inheritance of the Co-42 gene in SEL 1308. Black Magic, the susceptible parent of the mapping population, dies in five days after inoculation. Inoculum preparation, inoculation methods, and disease characterization of the segregating population were conducted as described by Young and Kelly (Plant Dis. 80:650–654 (1996)). Individual F2 plants from Black Magic/SEL 1308 population were screened with the SCAR marker SAS13 previously found to be linked to the Co-42 gene. Procedures for SCAR analysis are described by Melotto, M. et al. (Genome 39:1216–1219 (1996)). Additional RAPD markers flanking the Co-42 gene were sought by using bulked segregant analysis (Michelmore, R. W. et al., PNAS (USA) 88:9828–9832 (1991)). Inheritance of the disease phenotype and molecular markers was confirmed in 1018 F2 plants using the Chi-square test. Linkage analysis was performed using the Linkage-1 software (Suiter, K. A. et al., J. Hered. 74:203–204 (1983)) and distance between marker and resistance gene expressed in centiMorgan (cM) was calculated using Kosambi's function in the Linkage-1 program.

Southern analysis. Genomic DNA from bean cultivars and a BAC clone was digested with EcoR I according to the manufacturer (Boehringer Mannheim, Indianapolis, Ind.). Electrophoresis and blotting were conducted using standard techniques (Sambrook, J. et al., Molecular Cloning: A Laboratory Manual. 2nd Ed. Cold Spring Harbor Lab. Press, Plainview, N.Y. (1989)). The COK-4 gene was labeled using the DIG High Prime Starter kit I (Boehringer Mannheim) and used as a probe for hybridization. Stringency washes were performed in 2× SSC, 0.2% SDS and 0.2× SSC, 0.1% SDS solutions. Both washes were conducted twice for 30 minutes at 62° C.

Long distance PCR and primer walking. DNA clones flanking the SAS13 marker were generated using the Universal GenomeWalker™ kit (Clontech Laboratories, Inc., Palo Alto, Calif.). DNA from SEL 1308 was purified using phenol and chloroform, and digested with five restriction enzyme, Dra I, EcoR V, Pvu II, Sca I, and Stu I. Adaptors were ligated to restricted DNA samples for PCR amplification with adaptor-specific primers. PCR reactions were carried out in 50 ul solution containing 1× Advantage Genomic Polymerase Mix (Clontech Laboratories, Inc., Palo Alto, Calif.), 1.1 mM Mg(OAc)2, 10 mM of each dNTP, 10 pM of each adaptor-specific and SAS13 primers, and 50 ng of DNA template. PCR reactions were placed in a 9600 Thermocycler (Perkin Elmer Applied Biosystems) and the PCR file consisted of 7 cycles of 2 seconds at 94° C., 4 minutes at 70° C., followed by 32 cycles of 2 seconds at 94° C., 4 minutes at 65° C. and an extension cycle of 7 minutes at 65° C. Long distance PCR (LD-PCR) amplification products were cloned using the TOPO™ TA Cloning kit (Invitrogen Corp., San Diego, Calif.). Both strands of cloned DNA fragments were sequenced using an Applied Biosystems 377 DNA Sequencer (Perkin Elmer Applied Biosystems) as previously described by Melotto et al. (Genome 39:1216–1219 (1996)). New primers were designed based on those sequences to walk in uncloned genomic DNA as proposed by Siebert et al. (Nucleic Acid Res. 23:1087–1089 (1995)).

Results

The SCAR marker SAS13 was previously found to be tightly linked to the Co42 gene, which conditions resistance to anthracnose in common bean (Young, R. A. et al., Theor. Appl. Genet. 96:87–94 (1998)). The marker co-segregated with 1014 F2 individuals in a population size of 1018 (FIG. 1A). The 950-bp DNA fragment generated by the SAS13 marker was sequenced and analyzed for similarities to sequences of known disease resistance genes. The alignment obtained by using BLAST search software (Altschul, S. F. et al., Nucleic Acids Res. 25:3389–3402 (1997)) revealed a high similarity to serine-threonine kinase (STK) domains such as the ones encoded by the disease resistance gene Pto (gi|430992; gi|1809257; Martin, G. B. et al., Science 262:1432–1436 (1993)) and Fen gene (gi|1098334; Martin, G. B. et al., Plant Cell 6:1543–1552 (1994)) in tomato. Other proteins similar to the SAS13 DNA fragment included receptor-like kinases (RLK) from other organisms including Arabidopsis thaliana, Brassica sp, Oryza sativa, and Zea mays. Based on these results, the SAS13 marker was used as a starting point for primer walking in genomic DNA to find complete gene sequences encoding for protein kinase domains. Four overlapping clones extending the original SAS13 950-bp fragment were obtained and the full length of the contig included 3,371 bp. The full length contig is shown in FIG. 1B. The arrows indicate COK-4 specific primers and restriction sites are letter coded, B=Bam H, E=EcoR I, H=Hind II, K=Kpn I, Me=Mse I and Mp=Msp I. Primer pairs were designed to test whether the generated clones were contiguous in the plant genome. All primer sets amplified a single band of the predicted size. Sequence analysis of the contig revealed an open reading frame (ORF) of 1110 bp, which was named COK-4 (SEQ ID NO: 1; FIGS. 1B and 1C). Two essential eukaryote promoter elements, TATA and CAAT boxes, and putative promoter sequences were found upstream of the COK-4 gene. As shown in FIG. 2, the predicted amino acid sequence of COK-4 (SEQ ID NO: 3; a, FIG. 2) has a high degree of similarity with expressed sequences generated by the Pto gene from Lycopersicon pimpinellifolium and L. esculentum (38% identity, 53% similarity and 15% gap; Martin, G. B. et al., Science 262:1432–1436 (1993)), TMK protein from rice (29%, 45%, and 16%; van der Knaap, E. et al., Plant Physiol. 112:1397 (1996)), extracellular S-domain from Brassica oleracea (30%, 45%, 15%; PID:g2598271), S-domain receptor-like protein kinase from Z. mays (33%, 49%, 14%; PID:g3445397), and leucine-rich repeat (LRR) transmembrane protein kinase 2 from Z. mays (28%, 45%, 19%; Li, Z. et al., Plant Mol. Biol. 37:749–761 (1998)). In FIG. 2, amino acid identity is indicated by a double underline and amino acid similarity is indicated by a single underline. Numbers in the sequence indicate the first and last amino acids aligned. The amino acid sequences are: a) COK-4 (SEQ ID NO: 3), b) disease resistance protein kinase Pto (SEQ ID NO: 5), c) serine/threonine protein kinase Pto (Lycopersicon esculentum; SEQ ID NO: 6), d) putative serine/threonine protein kinase, Fen gene (L. esculentum; SEQ ID NO: 7), e) TMK (Oryza sativa; SEQ ID NO: 8), and f) extracellular S domain of Brassica oleracea (SEQ ID NO: 9). The protein encoded by COK-4 was analyzed for possible functional domains. The COK-4 protein has a STK domain, which includes a protein kinase ATP-binding region signature (amino acids 53 to 79), a primary transmembrane domain (amino acids 202 to 224), putative sites for N-myristoylation (amino acids 7 to 12, 149 to 154, 160 to 165, 250 to 255, and 364 to 369) and N-glycosylation (amino acids 16 to 18 and 26 to 28), and a cAMP and cGMP-dependent protein kinase site (amino acids 41 to 44) (SEQ ID NO: 3; FIG. 1C). The primary transmembrane region is indicated by the underlined amino acids (202 to 224) and the secondary transmembrane region by the wavy underlined amino acids (226 to 248 and 256 to 278) in FIG. 1C.

Discussion

Two lines of evidence strongly suggest that the COK-4 gene, herein described, is a member of the complex Co-42 locus conditioning resistance to anthracnose in common bean. First, genetic analysis indicated co-segregation of the COK-4 gene with the resistant phenotype in a population of 1350 F3 individuals. Secondly, amino acid sequence analysis of the COK-4 gene, which is located 462 bp downstream of the SAS13 marker (FIG. 1B), revealed high similarity with previously cloned resistance genes and protein domains known to play an important role in disease resistance. The putative protein encoded by the COK-4 gene has the structure of STKs and RLKs. Receptor-like kinases contain an extracellular domain possibly functioning in ligand binding and a cytoplasmic domain responsible for signal transduction (Walker, J. C., Pl. Mol. Biol. 26:1599–1609 (1994)). The COK-4 protein most likely is localized at the membrane because it contains three highly hydrophobic regions characteristic of a transmembrane domain and has an average hydrophobicity of −0.036 (calculated by the SOSUI software; Hirokawa, T. et al., Bioinformatics 14:378–379 (1998)). Alignment of the COK-4 amino acid sequence with the extracellular S-domain of Brassica oleracea and LRR transmembrane and RLK domain of Z. mays also supports localization of the COK-4 protein in the cellular membrane. If the resistance gene product is the receptor for the pathogen Avr gene product, it is expected that recognition occurs at the membrane level. Colletotrichum lindemuthianum is a hemibiotrophic fungus that penetrates the bean cell wall (Bailey, J. A. et al., Infection Strategies of Colletotrichum species. In: Bailey, J. A., Jeger. M. J. eds. Colletotrichum—Biology, Pathology and Control. Wallington, Oxon (U.K.), CAB International 88–120 (1992)). In addition, race specificity in C. lindemuthianum is expressed after fungal penetration through the epidermal cell wall and the primary hyphae of C. lindemuthianum remain external to the host plasma membrane, which becomes invaginated around the fungus (Bailey J. A. et al., Infection Strategies of Colletotrichum species. In: Bailey, J. A., Jeger. M. J. eds. Colletotrichum—Biology, Pathology and Control.

Wallington, Oxon (U.K.), CAB International 88–120 (1992)). These observations suggest that the avirulence gene product maybe a host-specific elicitor located in the membrane and pathogen recognition may occur at the surfaces of the *C. lindemuthianum* infection hyphae and bean cell membrane.

Most of the disease resistance genes previously cloned confer resistance to bacterial diseases and their products are localized in the cytoplasm. For instance, Pto is soluble protein localized in the cytoplasm of tomato cells where it binds to the AvrPto protein of the bacterial pathogen (Scofield, S. R. et al., Science 2063–2065 (1996); Tang, X. et al., Science 274:2060–2063 (1996)). Bacterial Avr gene products are known to be secreted into the host cytoplasm through the type III secretory system (Bent, A. F., The Plant Cell 8:1757–1771 (1996)). However, little is known about the function of Avr proteins from fungal pathogens and only a few fungal Avr-generated signals have been described. Race-specific elicitors have been partially purified from two hemibiotrophic plant pathogens, *Cladosporium fulvum* and *C. lindemuthianum* (Lamb, C. J. et al., Cell 56:215–224 (1989)). One well-studied example of race-cultivar specificity is the *C. fulvum/Lycopersicon* pathosystem. Cf proteins possess extracellular domains, which supposedly recognize the corresponding Avr proteins (Jones, D. A. et al., Science 266:789–793 (1994); Dixon, M. S. et al., Cell 84:451–459 (1996)). Although Avr proteins of *C. lindemuthianum* have not been isolated, occurrence of race-cultivar specificity suggests the presence of Avr-generated signal triggering plant defense response. Based on the similarities between the *C. fulvum*/tomato and *C. lindemuthianum*/bean pathosystems, one would expect that host-specific elicitors and anthracnose resistance gene products are located at the membrane where the pathogen is recognized.

SPECIFIC EXAMPLE 2

Restriction and Linkage Mapping of the Cok-4 Gene

Materials and Methods

Restriction analysis of specific PCR products. PCR primers were designed to amplify specific DNA fragments near the SAS13 marker region. The PCR amplification reaction contained 50 ng of genomic DNA, 10 mM of each dNTP, 10 pmol of each forward and reverse primers, lx enzyme buffer containing MgSO4 and 1U of Pfu DNA polymerase (Promega, Madison, Wis.). PCR reactions were placed in a 9600 Thermocycler (Perkin Elmer Applied Biosystems) and the PCR file consisted of 34 cycles of 20 seconds at 95° C., 30 seconds at 55° C., and 4 minutes at 72° C., followed by an extension cycle of 7 minutes at 72° C. The amplification product was used in a digestion reaction containing 1× enzyme buffer, 10 U of restriction enzyme and 10 µl of PCR reaction. Digestion of DNA fragment was carried out for four hours at 37° C. Restriction patterns were observed on 0.8% ethidium bromide-stained agarose gel.

TABLE 1

Sequence of the specific primer set designed to amplify the COK-4 gene in the vicinity of the Co-4$^2$ locus.

| Primer | Nucleotide position | Sequence (5'–3') |
|---|---|---|
| Forward | 405–426 | GTA TGG TAA GTG ACA AGT GAG A (SEQ ID NO:10) |

TABLE 1-continued

Sequence of the specific primer set designed to amplify the COK-4 gene in the vicinity of the Co-4$^2$ locus.

| Primer | Nucleotide position | Sequence (5'–3') |
|---|---|---|
| Reverse | 1578–1556 | ACC TGG TCA CTT ACA TTT CTT CA (SEQ ID NO:11) |

Figure 5:
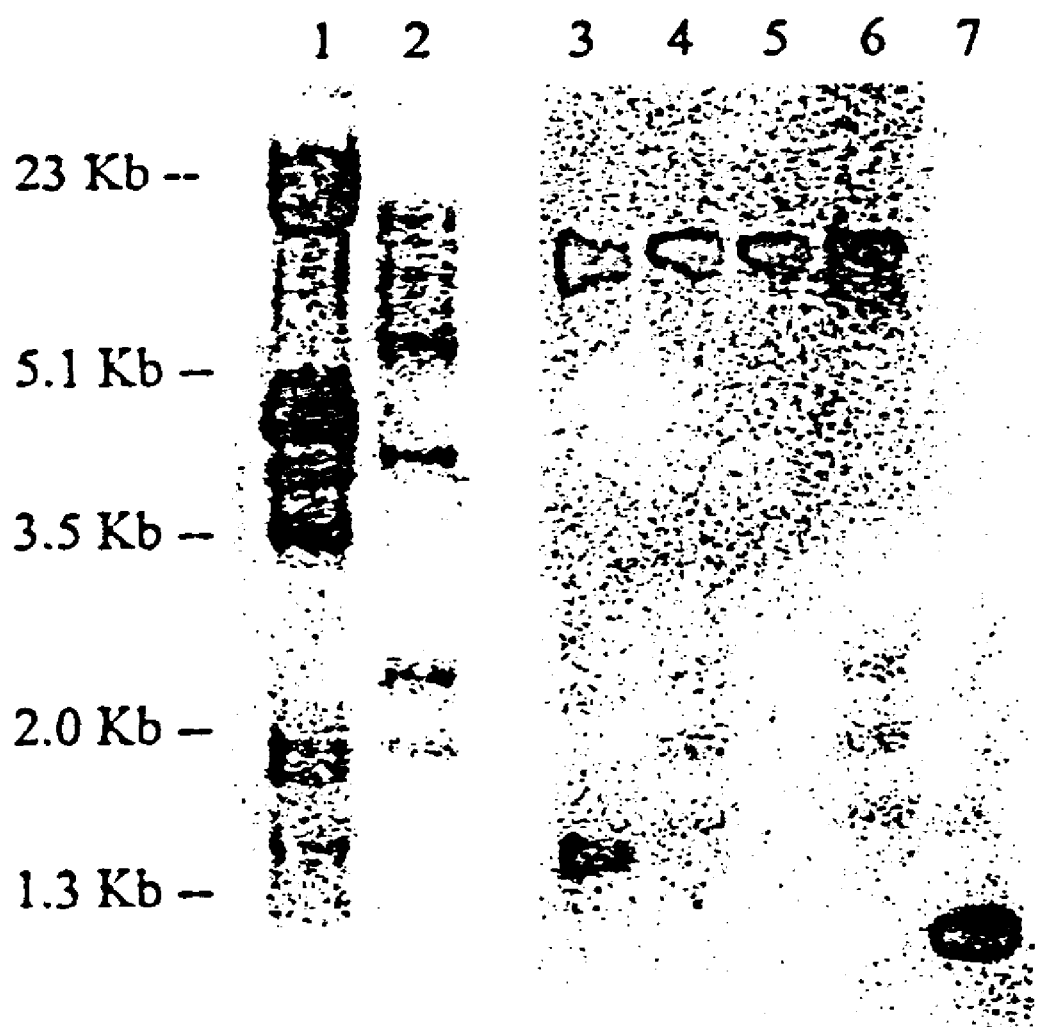
Figure 6:
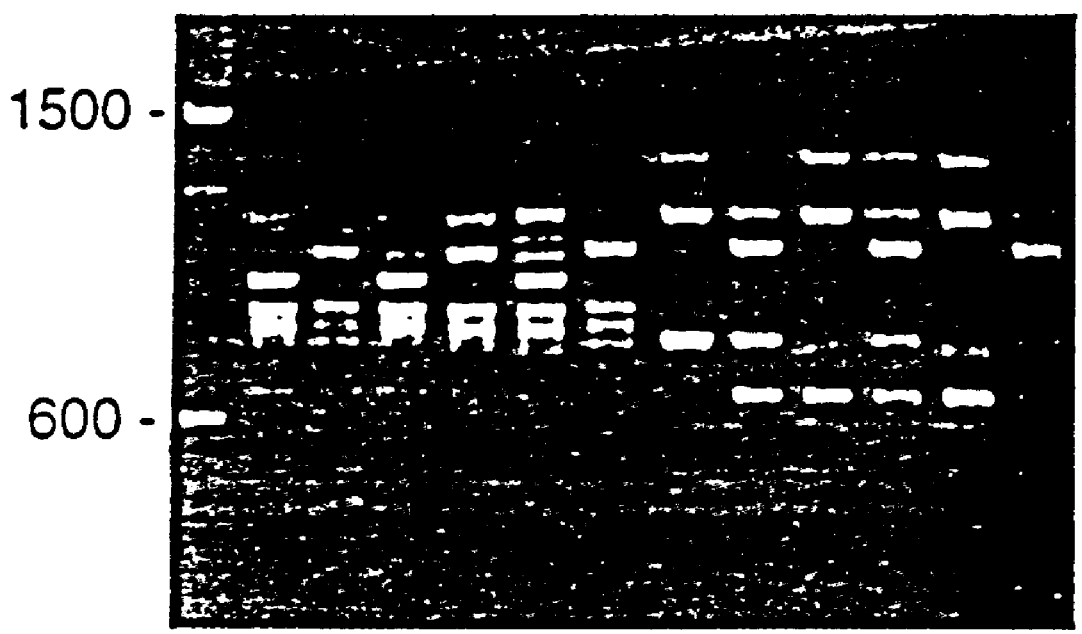

To determine the copy number of the COK-4 gene in different bean cultivars, EcoR I-restricted DNA was probed with the COK-4 gene clone (FIG. 5). The restriction enzyme EcoR I does not cut the COK-4 gene. The resistant cultivars SEL 1308 (Lane 3, FIG. 5), possessed two major homologous DNA sequences of 1.5 and 9 kb in size, whereas the susceptible cultivars SEL 1360 (Lane 6, FIG. 5) and Black Magic (Lane 4, FIG. 5) possessed multiple homologous sequences of various sizes. Again, TO possessed a unique RFLP pattern with only one 9-kb DNA fragment (Lane 5, FIG. 5). The BAC clone 7847 possessed at least four copies of the COK-4 ORF. A linkage map around the COK-4 gene could be predicted using two newly identified RAPD markers, OH181150 and OBB141150/1050. These markers are closely linked to the Co-42 gene and were identified by using bulked segregant analysis (Michelmore, R. W. et al., PNAS (USA) 88:9828–9832 (1991)). OH181150 is a dominant marker linked in coupling with the Co-42 locus at 1.11 cM, whereas OBB141150/1050 is a co-dominant marker, which amplifies a 1150-bp DNA band in the resistant parent SEL 1308 and a 1050-bp DNA band in the susceptible parent Black Magic (FIG. 6). The DNA of six bean cultivars was amplified with RAPD markers OBB141150/1050 (Lanes 2–7, FIG. 6) and OH181150 (Lanes 8–13, FIG. 6). The six bean cultivars were Black Magic (co-42/co-42; Lane 2, FIG. 6), SEL 1308 (Co-42/Co-42; Lane 3, FIG. 6), SEL 1360 (co42/co-42; Lane 4, FIG. 6), G2333 (Co-42/Co-42; Lane 5, FIG. 6), heterozygous resistant F2 individual (Lane 6, FIG. 6), homozygous resistant F2 individual (Lane 7, FIG. 6), Black Magic (Lane 8, FIG. 6), SEL 1308 (Lane 9, FIG. 6), SEL 1360 (Lane 10, FIG. 6), G2333 (Lane 11, FIG. 6), homozygous resistant F2 individual (Lane 12, FIG. 6) and homozygous susceptible F2 individual (co-42/co-42; Lane 13, FIG. 6). The OBB141150/1050 marker co-segregated with the Co-42 gene and is linked at 2.24 cM. Linkage analysis indicated that these markers flank the Co-42 gene and are 4.65 cM apart. A previously identified marker, OAL9780 appears closely associated with OH181150 at 5.8 cM (FIG. 1A).

Discussion

Although the COK-4 region was amplified in both resistant and susceptible parents of the mapping population, internal differences in nucleotide sequences exist as indicated by restriction (FIG. 3) and sequence (FIG. 4) analyses. Single nucleotide polymorphisms (SNPs) identified in the COK-4 sequences of resistant and susceptible bean lines and co-segregation of restriction patterns with disease phenotype, indicate that the COK-4 gene is involved in anthracnose resistance. Small variation in gene sequences can result in contrasting phenotypes. In tomato, the Pto and Fen genes are present in bacterial speck-susceptible and fenthion-sensitive genotypes and encode a protein kinase 87 and 98% identical to the resistance alleles, respectively (Jia, Y. et al., Plant Cell 9:61–73 (1997)). A SNP found in rice accounted for 80% of the variation in amylose content (Ayres, N. M. et al., Theor. Appl. Genet. 94:773–781 (1997)). The original SAS13 SCAR marker, which amplified a single 950-bp fragment in the resistant parent, co-segregated with the Co-42 resistance gene in the segregating population of 1018 F2 individuals. Four recombinant individuals were detected and the distance between the marker and the Co-42 locus was estimated at 0.39 cM. Three susceptible individuals possessing the SAS13 fragment and one resistant line lacking the fragment were observed. These four F2 individuals however, possessed the COK-4 allele corresponding to the phenotype of the plant confirmed by restriction analysis.

Previous genetic studies indicated that the Co-4 locus is a complex gene family (Young, R. A. et al., Theor. Appl. Genet. 96:87–94 (1998)). Two resistance alleles have been described which mapped at the Co-4 locus, one present in the bean cultivar TO and the other present in SEL 1308 as supported by allelism test and DNA sequence analysis. TO showed a unique restriction pattern and 44 SNPs at the COK-4 region compared to SEL 1308. Genetic analysis indicates a single gene segregating in the Black Magic/SEL 1308 F2 mapping population, however other genes may be tightly clustered at the Co-42 locus. Bean cultivars appear to possess multiple copies of the COK-4 gene based on Southern analysis. If the COK-4 homolog in TO is non-functional and different from that in SEL 1308, clearly the functional Co-4 gene in TO must be linked to COK-4 and may be a gene duplication based on the RFLP patterns. Another anthracnose resistance gene, Co-2 has also been shown to be a complex multigene family (Geffroy, V. et al., Theor. Appl. Genet. 96:494–502 (1998)). Sequence analysis of a linked marker revealed multiple copies of LRR sequences clustered near the Co-2 gene. Resistance genes appear to be clustered in the plant genome and may occur in multiple copies spanning large regions of the plant genome (Kesseli, R. V. et al., Mol. Pl. Microbe Interact. 6:722–728 (1993);
Maisonneuve, B. et al., Theor. Appl. Genet. 89:96–104 (1994); Meyers, B. C. et al., The Plant Cell 10:1817–1832 (1998)). The RAPD markers OH181150 and OBB141150/1050 are being used to further investigate the presence of the gene cluster and to locate the Co-4 gene in the integrated bean map (Freyre, R. et al., Theor. Appl. Genet. 97:847–856 (1998)) as they flank the entire locus.

These findings indicate that tightly linked molecular markers may be used to identify disease resistance gene candidates. The SAS13 marker tagged the Co-4 locus as it allowed the identification of different resistance alleles present in diverse bean cultivars. The marker was used to clone the COK-4 gene from resistant cultivars as well as homologs present in the susceptible cultivars. The COK-4 gene that conditions resistance to a fungal pathogen of common bean is a gene highly similar to the Pto resistance gene present in tomato. By comparing the COK-4 homologs, SNPs were identified and were more accurate than the SCAR marker in discriminating the plant genotype at the Co-4 locus. Most important, SNPs co-segregated with the disease phenotype in a large segregating population and could be used to identify three different alleles at the Co-4 locus. This work represents the first report of the successful cloning and molecular characterization of a disease resistance gene in grain legumes. Molecular cloning of resistance genes should facilitate studies on plant-pathogen interaction and ultimately facilitate genetic improvement of crop species.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

All patents and other publications cited herein are expressly incorporated by reference.

We claim:

1. An isolated nucleic acid comprising a nucleotide sequence encoding the polypeptide of SEQ ID NO: 3.

2. The isolated nucleic acid of claim 1 comprising the nucleotide sequence of SEQ ID NO: 1.

3. The isolated nucleic acid of claim 1 comprising the nucleotide sequence of SEQ ID NO: 2.

4. A vector comprising the nucleic acid of claim 2.

5. A host cell comprising the vector of claim 4.

6. The host cell of claim 5, wherein the host cell is a plant cell.

7. A vector comprising the nucleic acid of claim 3.

8. A host cell comprising the vector of claim 7.

9. The host cell of claim 8, wherein the host cell is a plant cell.

10. A method for conferring disease resistance to a plant comprising providing a plant into which has been introduced the nucleic acid of claim 1 and growing the plant, wherein the plant expresses the polypeptide encoded by the nucleic acid, thereby conferring disease resistance to the plant.

11. The method of claim 10, wherein the disease is a plant fungal disease.

12. The method of claim 11, wherein the plant fungal disease is anthracnose.

13. A transgenic plant comprising the nucleic acid of claim 1.

14. Transgenic seed of the plant of claim 13.

15. A transgenic plant produced by breeding the plant of claim 13, wherein the plant retains the trait of disease resistance.

16. Transgenic seed of the plant of claim 15.

17. A method for conferring disease resistance to a plant comprising introducing into the plant an isolated nucleic acid encoding the polypeptide comprising SEQ ID NO:3, wherein the nucleic acid comprises at least one restriction site for a restriction enzyme selected from the group consisting of Kpn I, Mse I and Msp I, wherein the plant expresses the polypeptide encoded by the nucleic acid, thereby conferring disease resistance to the plant.

18. A transgenic plant produced by the method of claim 17.

19. Transgenic seed of the plant of claim 18.

20. A transgenic plant produced by breeding the plant of claim 18, wherein the plant retains the trait of disease resistance.

21. Transgenic seed of the plant of claim 20.

22. A transgenic host cell comprising the isolated nucleic acid of claim 1.

23. The transgenic host cell of claim 22, wherein the host cell is a plant cell.

24. A transgenic plant comprising the plant cell of claim 23.

* * * * *

UNITED STATES PATENT AND TRADEMARK OFFICE
CERTIFICATE OF CORRECTION

PATENT NO. : 6,646,183 B2
DATED : November 11, 2003
INVENTOR(S) : James D. Kelly and Maeli Melotto It is certified that error appears in the above-identified patent and that said Letters Patent is hereby corrected as shown below:

Title page,
Item [75], Inventors, "Lansing, MI (US)" should be -- Piracaba-SP, Brazil --.

Column 3,
Line 30, "NO" should be -- NOS --.

Column 5,
Line 51, "thereof," should be -- thereof), --.

Column 7,
Line 17, "TOPOTM" should be -- TOPO™ --.
Line 39, "gil430992" should be -- gi|430992 --.
Line 39, "gil1809257" should be -- gi|1809257 --.
Line 40, "gil1098334" should be -- gi|1098334 --.
Line 53, "H=Hind II" should be -- H = Hind III --.

Column 9,
Line 36, "Cok-4" should be -- COK-4 --.

Signed and Sealed this

Seventh Day of June, 2005

JON W. DUDAS
*Director of the United States Patent and Trademark Office*

SEQUENCE LISTING

<160> NUMBER OF SEQ ID NOS: 11

<210> SEQ ID NO 1
<211> LENGTH: 1110
<212> TYPE: DNA
<213> ORGANISM: Phaseolus vulgaris

<400> SEQUENCE: 1

```
atgtttctga attgtgtggg catgtgttgt tcgaagccca caacaaatac aacttcatct      60
cagagacagt ttccaacgtt gatagaagag ctgtgccatc aatttctct caccgatctt      120 aggaaagcca ccaataactt tgatcagaag agagtaatag gaagtggatt atttagtgaa      180
gtatacaaag ggtgtctgca gcacgatggt gcttctgatt acacggtcgc aataaagcga      240
tttgattatc aaggatgggc agcgttcaac aaggaaatcg aattgctatg ccagcttcgt      300
caccctagat gtgtttctct tataggattc tgcaaccacg aaaatgagaa gattcttgta      360
tacgagtaca tgtccaatgg atctctagat aaacacctac aagaaggtca actatcatgg      420
aagaagaggc tggagatatg cataggagta gcacgtggac tacacttcct tcacaccgga      480
gccaagcgtt ccatctttca ctgtatcctc ggtcctggta ccgtcctttt ggatgaccag      540
atggagccaa aactcgctgg tttcgatgct agcgagcagg gatcacgttt tatgtcaaag      600
```

-continued

| | |
|---|---|
| cagaagcaaa tcaatgtgat cgtgttttgg gtaatttttg ttttgttgta tgagctcact | 660 |
| cactgccatg attttttgtg gatcaaacta agcttactct ttgttatagg ttgtaggggc | 720 |
| tacacggcta cggactatct catggatggt atcatcacag ctaaatggga tgttttctca | 780 |
| tttggtttcc ttctactaga agttgtgtgc aggaggatgt tttatttaat aactctgact | 840 |
| aaaaaagaat gtctggagaa tcctgttgag gagagaattg atccgattat caaggaaag | 900 |
| attgcaccag attgttggca agtgtttgta gatatgatgg taagttgctt gaagtatgaa | 960 |
| ccagatgaga gaccaacaat tggtgaagtg gaggtgcaac ttgagcatgc tctatccatg | 1020 |
| caggaacaat ctgatatcac aaactccaac tctgagtata ccttactctc caaaaccatt | 1080 |
| atttcccttg gagtgaagaa atgtaagtga | 1110 |

<210> SEQ ID NO 2
<211> LENGTH: 1090
<212> TYPE: DNA
<213> ORGANISM: Phaseolus vulgaris

<400> SEQUENCE: 2

| | |
|---|---|
| atgtttctga attgtgtggg catgtgttgt acgaagccca caacaaatac aacttcatct | 60 |
| cagagacagt ttccaacgtt gatagaagag ctgtgccatc aattttctct ctccgatctt | 120 |
| aggaaagcca tcaataactt tgatcagaag agagtaatag gaagtggatt ttttagggaa | 180 |
| gtatattaag ggtgtctgca gcatgatggt gcttctgatt acacggtcgc aataaagcga | 240 |
| tttgattatc aaggatggga agcgttcaac aaggaaatcg aattgctatg ccagcttcgt | 300 |
| caccctagat gtgtttctct tataggattc tgcaaccacc aaaatgagaa gattcttgta | 360 |
| tacgagtaca tgtccaatgg atctctagat aaacacctac aagatggtga actatcatgg | 420 |
| aagaagaggc tagagatctg cataggagta gcacgtggac tacactacct tcacactggt | 480 |
| gccaagcgtt ccatctttca ctgtatcctc ggtcctagta ccatccttt ggatgaccaa | 540 |
| atggagccaa aactcgctgg tttcggtgtt agcatgcagg gatcacgttt tatgtcaaag | 600 |
| cagaagcaaa tcaatgtaga tcgtgttttg ggtaattttt gttttgttgt atgagctcac | 660 |
| tcactgcaat gaattttgt ggatcaaact aagctaatac tctttgttat aggtactttt | 720 |
| ggctacccgg ctacggacta tgtcatggat ggtaccatca cagctaaatg ggatgttttc | 780 |
| tcatttggtt tccttctact agaagttgtg tgcaggagga tgttttattt gataactctg | 840 |
| actaaaaaaa aatgtctgga gaatcctgtt gaggagagaa ttgatccgat tatcaaaggg | 900 |
| aagattgcac cagattgttg gcaagtgttt gtagatatga tggtaacttg cttgaagtat | 960 |
| gaaccagatg agcgaccaac aattggtgaa gtggaggtgc aacttgagca tgctctatcc | 1020 |
| atgcaggaac aagctgatat cacaaactcc aactctgagt ataccttact gtccaaaacc | 1080 |
| attatttccc | 1090 |

<210> SEQ ID NO 3
<211> LENGTH: 369
<212> TYPE: PRT
<213> ORGANISM: Phaseolus vulgaris

<400> SEQUENCE: 3

Met Phe Leu Asn Cys Val Gly Met Cys Cys Ser Lys Pro Thr Thr Asn
 1               5                  10                  15

Thr Thr Ser Ser Gln Arg Gln Phe Pro Thr Leu Ile Glu Glu Leu Cys
             20                  25                  30

```
His Gln Phe Ser Leu Thr Asp Leu Arg Lys Ala Thr Asn Asn Phe Asp
         35                  40                  45

Gln Lys Arg Val Ile Gly Ser Gly Leu Phe Ser Glu Val Tyr Lys Gly
 50                  55                  60

Cys Leu Gln His Asp Gly Ala Ser Asp Tyr Thr Val Ala Ile Lys Arg
 65                  70                  75                  80

Phe Asp Tyr Gln Gly Trp Ala Ala Phe Asn Lys Glu Ile Glu Leu Leu
                 85                  90                  95

Cys Gln Leu Arg His Pro Arg Cys Val Ser Leu Ile Gly Phe Cys Asn
             100                 105                 110

His Glu Asn Glu Lys Ile Leu Val Tyr Glu Tyr Met Ser Asn Gly Ser
         115                 120                 125

Leu Asp Lys His Leu Gln Glu Gly Gln Leu Ser Trp Lys Lys Arg Leu
 130                 135                 140

Glu Ile Cys Ile Gly Val Ala Arg Gly Leu His Phe Leu His Thr Gly
145                 150                 155                 160

Ala Lys Arg Ser Ile Phe His Cys Ile Leu Gly Pro Gly Thr Val Leu
                 165                 170                 175

Leu Asp Asp Gln Met Glu Pro Lys Leu Ala Gly Phe Asp Ala Ser Glu
             180                 185                 190

Gln Gly Ser Arg Phe Met Ser Lys Gln Lys Gln Ile Asn Val Ile Val
         195                 200                 205

Phe Trp Val Ile Phe Val Leu Leu Tyr Glu Leu Thr His Cys His Asp
 210                 215                 220

Phe Leu Trp Ile Lys Leu Ser Leu Leu Phe Val Ile Gly Cys Arg Gly
225                 230                 235                 240

Tyr Thr Ala Thr Asp Tyr Leu Met Asp Gly Ile Ile Thr Ala Lys Trp
                 245                 250                 255

Asp Val Phe Ser Phe Gly Phe Leu Leu Leu Glu Val Val Cys Arg Arg
             260                 265                 270

Met Phe Tyr Leu Ile Thr Leu Thr Lys Lys Glu Cys Leu Glu Asn Pro
         275                 280                 285

Val Glu Glu Arg Ile Asp Pro Ile Ile Lys Gly Lys Ile Ala Pro Asp
 290                 295                 300

Cys Trp Gln Val Phe Val Asp Met Met Val Ser Cys Leu Lys Tyr Glu
305                 310                 315                 320

Pro Asp Glu Arg Pro Thr Ile Gly Glu Val Glu Val Gln Leu Glu His
                 325                 330                 335

Ala Leu Ser Met Gln Glu Gln Ser Asp Ile Thr Asn Ser Asn Ser Glu
             340                 345                 350

Tyr Thr Leu Leu Ser Lys Thr Ile Ile Ser Leu Gly Val Lys Lys Cys
         355                 360                 365

Lys

<210> SEQ ID NO 4
<211> LENGTH: 1111
<212> TYPE: DNA
<213> ORGANISM: Phaseolus vulgaris

<400> SEQUENCE: 4
atgtttctga attgtgtggg catgtgttgt tcgaagccca caacaaatac aacttcatct      60
cagagacagt ttccaacgtt gatagaagag ctgtgccatc aatttctct caccgatctt     120 aggaaagcca ccaataactt tgatcagaag agagtaatag gaagtggatt atttagtgaa     180
```

-continued

```
gtatacaaag ggtgtctgca gcatgatggt gcttctgatt acacggtcgc aataaagcga    240
tttgattatc aaggatgggc agcgttcaac aaggaaatcg aattgctatg ccagcttcgt    300
caccctagat gtgtttctct ataggattc agcaaccacg aaaatgagaa gattcttgta     360
tacgagtaca tgtccaatgg atctctagat aaacacctac aagaaggtca actatcatgg    420
aagaagaggc tagagatatg cataggagta gcacgtggac tacactacct tcacaccgga    480
gccaagcgtt ccatctttca ctgtatcctc ggtcctggta ccgtcctttt ggatgaccag    540
atggagccaa aactcgctgg tttcggtgct agcgagcagg gatcacgttt tatgtcaaag    600
cagaagcaaa tcaatgtaga tcgtgttttg ggtaattttt gttttttgt atgagctcac     660 tcactgccat gattttttgt ggatcaaact aagcttactc tttgttatag gttgttgggg    720
ctacacggct acggactatc tcatggatgg tatcatcaca gctaaatggg atgttttctc    780
atttggtttc cttctactag aagttgtgtg caggaggatg ttttatttga taactctgac    840
taaaaaaaaa tgtctggaga atcctgttga gtagagaatt gatccgatta tcaaagggaa    900
gattgcacca gattgttggc aagtgtttgt agatatgatg gtaacttgct tgaagtataa    960
accagatgag agaccaacaa ttggtgaagt ggaggtgcaa cttgagcatg ctctatccat   1020
gcaggaacaa gctgatatca caaactccaa ctctgagtat actttactgt ccaaaaccat   1080
tatttccctg ggagtgaaga aatgtaagtg a                                  1111
```

<210> SEQ ID NO 5
<211> LENGTH: 310
<212> TYPE: PRT
<213> ORGANISM: Lycopersicon esculentum

<400> SEQUENCE: 5

```
Thr Asn Ser Ile Asn Asp Ala Leu Ser Ser Tyr Leu Val Pro Phe
  1               5                  10                  15

Glu Ser Tyr Arg Val Pro Leu Val Asp Leu Glu Ala Thr Asn Asn
             20                  25                  30

Phe Asp His Lys Phe Leu Ile Gly His Gly Val Phe Gly Lys Val Tyr
         35                  40                  45

Lys Gly Val Leu Arg Asp Gly Ala Lys Val Ala Leu Lys Arg Arg Thr
     50                  55                  60

Pro Glu Ser Ser Gln Gly Ile Glu Glu Phe Glu Thr Glu Ile Glu Thr
 65                  70                  75                  80

Leu Ser Phe Cys Arg His Pro His Leu Val Ser Leu Ile Gly Phe Cys
                 85                  90                  95

Asp Glu Arg Asn Glu Met Ile Leu Ile Tyr Lys Tyr Met Glu Asn Gly
            100                 105                 110

Asn Leu Lys Arg His Leu Tyr Gly Ser Asp Leu Pro Thr Met Ser Met
        115                 120                 125

Ser Trp Glu Gln Arg Leu Glu Ile Cys Ile Gly Ala Ala Arg Gly Leu
    130                 135                 140

His Tyr Leu His Thr Arg Ala Ile Ile His Arg Asp Val Lys Ser Ile
145                 150                 155                 160

Asn Ile Leu Leu Asp Glu Asn Phe Val Pro Lys Ile Thr Asp Phe Gly
                165                 170                 175

Ile Ser Lys Lys Gly Thr Glu Leu Asp Gln Thr His Leu Ser Thr Val
            180                 185                 190

Val Lys Gly Thr Leu Gly Tyr Ile Asp Pro Glu Tyr Phe Ile Lys Gly
        195                 200                 205
```

```
Arg Leu Thr Glu Lys Ser Asp Val Tyr Ser Phe Gly Val Val Leu Phe
        210                 215                 220

Glu Val Leu Cys Ala Arg Ser Ala Ile Val Gln Ser Leu Pro Arg Glu
225                 230                 235                 240

Met Val Asn Leu Ala Glu Trp Ala Val Glu Ser His Asn Asn Gly Gln
                    245                 250                 255

Leu Glu Gln Ile Val Asp Pro Asn Leu Ala Asp Lys Ile Arg Pro Glu
                260                 265                 270

Ser Leu Arg Lys Phe Gly Asp Thr Ala Val Lys Cys Leu Ala Leu Ser
        275                 280                 285

Ser Glu Asp Arg Pro Ser Met Gly Asp Val Leu Trp Lys Leu Glu Tyr
290                 295                 300

Ala Leu Arg Leu Gln Glu
305                 310

<210> SEQ ID NO 6
<211> LENGTH: 308
<212> TYPE: PRT
<213> ORGANISM: Lycopersicon esculentum

<400> SEQUENCE: 6

Met Gly Ser Lys Tyr Ser Lys Ala Thr Asn Ser Ile Ser Asp Ala Ser
1               5                   10                  15

Asn Ser Phe Glu Ser Tyr Arg Phe Pro Leu Glu Asp Leu Glu Glu Ala
                20                  25                  30

Thr Asn Asn Phe Asp Asp Lys Phe Ile Gly Glu Gly Ala Phe Gly
            35                  40                  45

Lys Val Tyr Lys Gly Val Leu Arg Asp Gly Thr Lys Val Ala Leu Lys
50                  55                  60

Arg Gln Asn Arg Asp Ser Arg Gln Gly Ile Glu Glu Phe Gly Thr Glu
65                  70                  75                  80

Ile Gly Ile Leu Ser Arg Arg Ser His Pro His Leu Val Ser Leu Ile
                85                  90                  95

Gly Tyr Cys Asp Glu Arg Asn Glu Met Val Leu Ile Tyr Asp Tyr Met
            100                 105                 110

Glu Asn Gly Asn Leu Lys Ser His Leu Thr Gly Ser Asp Leu Pro Ser
        115                 120                 125

Met Ser Trp Glu Gln Arg Leu Glu Ile Cys Ile Gly Ala Ala Arg Gly
130                 135                 140

Leu His Tyr Leu His Thr Asn Gly Val Met His Arg Asp Val Lys Ser
145                 150                 155                 160

Ser Asn Ile Leu Leu Asp Glu Asn Phe Val Pro Lys Ile Thr Asp Phe
                165                 170                 175

Gly Leu Ser Lys Thr Arg Pro Gln Leu Tyr Gln Thr Thr Asp Val Lys
            180                 185                 190

Gly Thr Phe Gly Tyr Ile Asp Pro Glu Tyr Phe Ile Lys Gly Arg Leu
        195                 200                 205

Thr Glu Lys Ser Asp Val Tyr Ser Phe Gly Val Val Leu Phe Glu Val
210                 215                 220

Leu Cys Ala Arg Ser Ala Met Val Gln Ser Leu Pro Arg Glu Met Val
225                 230                 235                 240

Asn Leu Ala Glu Trp Ala Val Glu Ser His Asn Asn Gly Gln Leu Glu
                245                 250                 255

Gln Ile Val Asp Pro Asn Leu Ala Asp Lys Ile Arg Pro Glu Ser Leu
            260                 265                 270
```

-continued

```
Arg Lys Phe Gly Glu Thr Ala Val Lys Cys Leu Ala Leu Ser Ser Glu
            275                 280                 285

Asp Arg Pro Ser Met Gly Asp Val Leu Trp Lys Leu Glu Tyr Ala Leu
            290                 295                 300

Arg Leu Gln Glu
305

<210> SEQ ID NO 7
<211> LENGTH: 286
<212> TYPE: PRT
<213> ORGANISM: Lycopersicon esculentum

<400> SEQUENCE: 7

Tyr Arg Val Pro Phe Val Asp Leu Glu Glu Ala Thr Asn Asn Phe Asp
  1               5                  10                  15

Asp Lys Phe Phe Ile Gly Glu Gly Phe Gly Lys Val Tyr Arg Gly
             20                  25                  30

Val Leu Arg Asp Gly Thr Lys Val Ala Leu Lys Lys His Lys Arg Glu
             35                  40                  45

Ser Ser Gln Gly Ile Glu Glu Phe Glu Thr Glu Ile Glu Ile Leu Ser
      50                  55                  60

Phe Cys Ser His Pro His Leu Val Ser Leu Ile Gly Phe Cys Asp Glu
 65                  70                  75                  80

Arg Asn Glu Met Ile Leu Ile Tyr Asp Tyr Met Glu Asn Gly Asn Leu
                 85                  90                  95

Lys Ser His Leu Tyr Gly Ser Asp Leu Pro Thr Met Ser Met Ser Trp
            100                 105                 110

Glu Gln Arg Leu Glu Ile Cys Ile Gly Ala Ala Arg Gly Leu His Tyr
        115                 120                 125

Leu His Thr Asn Gly Val Ile His Arg Asp Val Lys Cys Thr Asn Ile
    130                 135                 140

Leu Leu Asp Glu Asn Phe Val Pro Lys Ile Thr Asp Phe Gly Ile Ser
145                 150                 155                 160

Lys Thr Met Pro Glu Leu Asp Leu Thr His Leu Ser Thr Val Val Arg
                165                 170                 175

Gly Asn Ile Gly Tyr Ile Ala Pro Glu Tyr Ala Leu Trp Gly Gln Leu
            180                 185                 190

Thr Glu Lys Ser Asp Val Tyr Ser Phe Gly Val Val Leu Phe Glu Val
        195                 200                 205

Leu Cys Ala Arg Pro Ala Leu Tyr Leu Ser Glu Met Met Ser Ser Asp
    210                 215                 220

Asp Glu Thr Gln Lys Met Gly Gln Leu Glu Gln Ile Val Asp Pro Ala
225                 230                 235                 240

Ile Ala Ala Lys Ile Arg Pro Gly Ser Leu Arg Met Phe Gly Glu Thr
                245                 250                 255

Ala Met Lys Cys Leu Ala Pro Ser Ser Lys Asn Arg Pro Ser Met Gly
            260                 265                 270

Asp Val Leu Trp Lys Leu Glu Tyr Ala Leu Cys Leu Gln Glu
            275                 280                 285

<210> SEQ ID NO 8
<211> LENGTH: 339
<212> TYPE: PRT
<213> ORGANISM: Oryza sativa
```

-continued

```
<400> SEQUENCE: 8

Asn Val Asn Gly Gly Ala Ala Ser Glu Thr Tyr Ser Gln Ala Ser
  1               5                  10                  15

Ser Gly Pro Arg Asp Ile His Val Glu Thr Gly Asn Met Val Ile
             20                  25                  30

Ser Ile Gln Val Leu Arg Asn Val Thr Asn Asn Phe Ser Asp Glu Asn
         35                  40                  45

Val Leu Gly Arg Gly Gly Phe Gly Thr Val Tyr Lys Gly Glu Leu His
     50                  55                  60

Asp Gly Thr Lys Ile Ala Val Lys Arg Met Glu Ala Gly Val Met Gly
 65                  70                  75                  80

Asn Lys Gly Leu Asn Glu Phe Lys Ser Glu Ile Ala Val Leu Thr Lys
                 85                  90                  95

Val Arg His Arg Asn Leu Val Ser Leu Leu Gly Tyr Cys Leu Asp Gly
            100                 105                 110

Asn Glu Arg Ile Leu Val Tyr Glu Tyr Met Pro Gln Gly Thr Leu Ser
            115                 120                 125

Gln His Leu Phe Glu Trp Lys Glu His Asn Leu Arg Pro Leu Glu Trp
    130                 135                 140

Lys Lys Arg Leu Ser Ile Ala Leu Asp Val Ala Arg Gly Val Glu Tyr
145                 150                 155                 160

Leu His Ser Leu Ala Gln Gln Thr Phe Ile His Arg Asp Leu Lys Pro
                165                 170                 175

Ser Asn Ile Leu Leu Gly Asp Asp Met Lys Ala Lys Val Ala Asp Phe
            180                 185                 190

Gly Leu Val Arg Leu Ala Pro Ala Asp Gly Lys Cys Val Ser Val Glu
        195                 200                 205

Thr Arg Leu Ala Gly Thr Phe Gly Tyr Leu Ala Pro Glu Tyr Ala Val
    210                 215                 220

Thr Gly Arg Val Thr Thr Lys Ala Asp Val Phe Ser Phe Gly Val Ile
225                 230                 235                 240

Leu Met Glu Leu Ile Thr Gly Arg Lys Ala Leu Asp Glu Thr Gln Pro
                245                 250                 255

Glu Asp Ser Met His Leu Val Thr Trp Phe Arg Arg Met Gln Leu Ser
            260                 265                 270

Lys Asp Thr Phe Gln Lys Ala Ile Asp Pro Thr Ile Asp Leu Thr Glu
        275                 280                 285

Glu Thr Leu Ala Ser Val Ser Thr Val Ala Glu Leu Ala Gly His Cys
    290                 295                 300

Cys Ala Arg Glu Pro His Gln Arg Pro Asp Met Gly His Ala Val Asn
305                 310                 315                 320

Val Leu Ser Thr Leu Ser Asp Val Trp Lys Pro Ser Asp Pro Asp Ser
                325                 330                 335

Asp Asp Ser

<210> SEQ ID NO 9
<211> LENGTH: 280
<212> TYPE: PRT
<213> ORGANISM: Brassica oleracea

<400> SEQUENCE: 9

Ala Thr Asn Asn Phe Ser Ser Ala Asn Lys Leu Gly Arg Gly Gly Phe
  1               5                  10                  15
```

```
Gly Thr Val Tyr Lys Gly Arg Leu Leu Asp Gly Lys Glu Ile Ala Val
            20                  25                  30

Lys Arg Leu Ser Lys Met Ser Leu Gln Gly Thr Asp Glu Phe Lys Asn
        35                  40                  45

Glu Val Lys Leu Ile Ala Arg Leu Gln His Ile Asn Leu Val Arg Leu
    50                  55                  60

Ile Gly Cys Cys Ile Asp Lys Gly Glu Lys Met Leu Ile Tyr Glu Tyr
65                  70                  75                  80

Leu Glu Asn Leu Ser Leu Asp Ser His Ile Phe Asp Ile Thr Arg Arg
                85                  90                  95

Ser Asn Leu Asn Trp Gln Met Arg Phe Asp Ile Thr Asn Gly Ile Ala
            100                 105                 110

Arg Gly Leu Val Tyr Leu His Arg Asp Ser Arg Phe Met Ile Ile His
        115                 120                 125

Arg Asp Leu Lys Ala Ser Asn Val Leu Leu Asp Lys Asn Met Thr Pro
130                 135                 140

Lys Ile Ser Asp Phe Gly Met Ala Arg Ile Phe Gly Arg Asp Asp Ala
145                 150                 155                 160

Glu Ala Asn Thr Arg Lys Val Val Gly Thr Tyr Gly Tyr Met Ser Pro
                165                 170                 175

Glu Tyr Ala Met Asp Gly Ile Phe Ser Met Lys Ser Asp Val Phe Ser
            180                 185                 190

Phe Gly Val Leu Leu Leu Glu Ile Ile Ser Gly Lys Lys Asn Asn Gly
        195                 200                 205

Phe Tyr Asn Ser Asn Gln Asp Leu Asn Leu Leu Ala Leu Val Trp Arg
    210                 215                 220

Lys Trp Lys Glu Gly Lys Trp Leu Glu Ile Leu Asp Pro Ile Ile Ile
225                 230                 235                 240

Asp Ser Ser Ser Thr Gly Gln Ala His Glu Ile Leu Arg Cys Ile
                245                 250                 255

Gln Ile Gly Leu Leu Cys Val Gln Glu Arg Ala Glu Asp Arg Pro Val
            260                 265                 270

Met Ala Ser Val Met Val Met Ile
        275                 280

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence:synthetic
      oligonucleotide primer

<400> SEQUENCE: 10
gtatggtaag tgacaagtga ga                                              22

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence:synthetic
      oligonucleotide primer

<400> SEQUENCE: 11
acctggtcac ttacatttct tca                                             23
```